US009018263B2

(12) United States Patent
Fenyvesi et al.

(10) Patent No.: US 9,018,263 B2
(45) Date of Patent: Apr. 28, 2015

(54) ANTIMICROBIAL COMPOSITIONS COMPRISING TRIMETHYLENE GLYCOL OLIGOMER AND METHODS OF USING THE COMPOSITIONS

(75) Inventors: Gyorgyi Fenyvesi, Wilmington, DE (US); Hari Babu Sunkara, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 330 days.

(21) Appl. No.: 13/047,103

(22) Filed: Mar. 14, 2011

(65) Prior Publication Data

US 2011/0224307 A1    Sep. 15, 2011

Related U.S. Application Data

(60) Provisional application No. 61/313,923, filed on Mar. 15, 2010.

(51) Int. Cl.
| | |
|---|---|
| *A61K 31/01* | (2006.01) |
| *A61K 31/045* | (2006.01) |
| *A61K 31/047* | (2006.01) |
| *A61K 31/075* | (2006.01) |
| *C07C 43/13* | (2006.01) |
| *A01N 31/02* | (2006.01) |

(52) U.S. Cl.
CPC ............. *C07C 43/132* (2013.01); *A61K 31/047* (2013.01); *A61K 31/01* (2013.01); *A61K 31/045* (2013.01); *A61K 31/075* (2013.01); *A01N 31/02* (2013.01)

(58) Field of Classification Search
CPC ... A61K 31/01; A61K 31/045; A61K 31/047; A61K 31/075
USPC ........................................................ 514/723
See application file for complete search history.

(56) References Cited

U.S. PATENT DOCUMENTS

| | | | | |
|---|---|---|---|---|
| 3,911,133 A | * | 10/1975 | Edwards ..................... | 514/397 |
| 4,232,041 A | | 11/1980 | Burk et al. | |
| 5,847,047 A | | 12/1998 | Haynie | |
| 7,582,681 B2 | | 9/2009 | Schmaus et al. | |
| 7,628,999 B2 | | 12/2009 | Sunkara | |
| 2008/0175875 A1 | | 7/2008 | Sunkara | |
| 2009/0092569 A1 | | 4/2009 | Sunkara | |
| 2009/0169500 A1 | | 7/2009 | Sunkara | |
| 2009/0175806 A1 | | 7/2009 | Modak et al. | |
| 2009/0286878 A1 | | 11/2009 | Elder et al. | |

OTHER PUBLICATIONS

Newman et al. ("High-Dilution Cyclization of Polyoxapentacosanodinitriles" J. Org. Chem., vol. 40, No. 20, 1975, 2863-2870).*
Related U.S. Appl. No. 11/801,872, Hari Babu Sunkara, filed Dec. 8, 2009 (U.S. Publication No. US-2007-0269392, Published Nov. 22, 2007), Now US Patent No. 7,628,999.
Related U.S. Appl. No. 12/400,309, Hari Babu Sunkara, filed Mar. 9, 2009 (U.S. Publication No. US-2009-0169500-A, Published Jul. 2, 2009).
Related U.S. Appl. No. 11/859,091, Hari Babu Sunkara, filed Sep. 21, 2007 (U.S. Publication No. US-2008-0175875-A1, Published Jul. 24, 2008).
Related U.S. Appl. No. 11/869,056, Hari Babu Sunkara, filed Nov. 9, 2007 (U.S. Publication No. US-2009-0092569-A1, Published Apr. 9, 2009).
Related U.S. Appl. No. 12/938,452, Hari Babu Sunkara, filed Nov. 3, 2010.
F.M. Berger et al., The Antimicrobial Action of Certain Glycerol Ethers and Related Compounds, Appl. Microbiol. (1953), pp. 146-149.
T. McEntee, Industrial Antimicrobial Agents (Standard Article), Kirk-Othmer Encyclopedia of Chemical Technology (1995), Article On-Line Posting Date Dec. 4, 2000, pp. 1-18.
International Search Report, PCT International Application No. PCT/US2011/028257, Mailed Nov. 29, 2011.
L. Kunlayakorn et al., Antimicrobial Efficacy of Caprylyl Glycol and Ethylhexylglycerine in Emulsion, J. Health Res., vol. 23, No. 1 (2009), pp. 1-3.
A. V. Bailey et al., Antimicrobial Properties of Some Mixed Diesters of Aliphatic Diols, J. Am. Oil Chem. Soc., vol. 53, No. 10 (1976), pp. 632-633.

* cited by examiner

*Primary Examiner* — Yong Chong (57) ABSTRACT

Disclosed are antimicrobial compositions, and methods for killing, inhibiting, or preventing the growth of microbes, using trimethylene glycol oligomers or dimers. The trimethylene glycol oligomers and dimers have the formula $R(CH_2CH_2CH_2-O-CH_2CH_2CH_2)_nR^1$ where R and $R^1$ are hydroxyl, amine, or ester functionalitiess, and n is 2 or higher. The antimicrobial compositions are useful in personal care and cosmetic compositions.

8 Claims, 6 Drawing Sheets

ANTIMICROBIAL COMPOSITIONS COMPRISING TRIMETHYLENE GLYCOL OLIGOMER AND METHODS OF USING THE COMPOSITIONS

CROSS-REFERENCE TO RELATED APPLICATION

This application claims the benefit of priority of U.S. Provisional Application No. 61/313,923 filed on Mar. 15, 2010.

FIELD OF THE INVENTION

The invention relates to the field of antimicrobial agents and preservatives. More specifically, the invention relates to antimicrobial compositions, and methods for killing, inhibiting, or preventing the growth of microbes, using trimethylene glycol oligomer or dimer.

BACKGROUND

Antimicrobial agents and preservatives have been used to kill or inhibit the growth of harmful microorganisms. Commonly used agents include parabens, esters of p-benzoic acid, formaldehyde releasers, isothiazolinones, organic acids, and organic alcohols. Some issues that arise when choosing an agent for a particular application include biocide tolerance, public perception, toxicity (including skin irritation or sensitization), incompatibility or insolubility with other ingredients in the formulation, stability, deactivation by pH, and odor. In response, nonconventional agents have been studied such as 1,2-alkanediols, phospholipids, benzoic/sorbic acids, essential oils and other natural materials.

U.S. Pat. No. 7,582,681 discloses the use for antimicrobial action of mixtures of two, three or more straight-chain 1,2-alkanediols, the chains lengths of which (i) are different and (ii) in each case are in the range of 5 to 10 carbon atoms.

Natural or naturally derived antimicrobial ingredients are preferred for many applications. However, there is a limited availability of natural materials suitable for antimicrobial compositions. There is also an environmental advantage for manufacturers to provide products of renewably based sources.

Thus, there exists a need for antimicrobial compositions containing ingredients derived from renewable resources, which are non-skin irritating, safe, and effective for repeated use in various applications against a broad spectrum of microorganisms at minimal amounts.

SUMMARY OF THE INVENTION

One aspect of the present invention is an antimicrobial composition comprising at least 0.1 total weight percent of one or more trimethylene glycol oligomers of formula $R(CH_2CH_2CH_2-O-CH_2CH_2CH_2)_nR^1$ wherein R and $R^1$ are each independently hydroxyl, amine, or ester functionalities, and n is 2 or higher, wherein the trimethylene glycol oligomer has molecular weight less than about 650.

Another aspect of the present invention is a method for killing, inhibiting, or preventing the growth of at least one microbe in a composition, the method comprising adding to the composition one or more of a trimethylene glycol oligomer of the formula $R(CH_2CH_2CH_2-O-CH_2CH_2CH_2)_nR^1$ wherein R and $R^1$ are each independently hydroxyl, amine, or ester functionalities, and n is 2 or higher.

DETAILED DESCRIPTION

By "antimicrobial composition" is meant a composition that comprises one or more antimicrobial agents or preservatives. An antimicrobial agent kills, inhibits, or prevents the growth of microbes. Antimicrobial agents that inhibit or prevent the growth of microbes are known as bacteriostatic, while agents that kill microbes are known as bactericidal. Antimicrobial agents include antibacterial, antiviral, antifungal and antiparisitic agents. A preservative is a natural or synthetic chemical that is added to products such as foods, cosmetics or pharmaceuticals to prevent spoilage. Similar to antimicrobials, preservatives prevent the growth of molds, yeasts and bacteria. By "microbe" is meant any microorganism such as bacteria, including gram-negative and gram-positive bacteria, yeasts, algaes, and molds.

According to one embodiment, there are provided antimicrobial compositions comprising one or more of a trimethylene glycol oligomer of the formula $R(CH_2CH_2CH_2-O-CH_2CH_2CH_2)_nR^1$ wherein R and $R^1$ are each independently hydroxyl, amine, or ester functionalities, and n is 2 or higher. In some embodiments, R and $R^1$ are the same. In one embodiment, R and $R^1$ are hydroxyl.

In one embodiment, the antimicrobial composition comprises at least 10 weight percent of the polytrimethylene ether glycol with an average molecular weight of less than 650, or ranging from about 250 to about 650, and a polydispersity ranging from about 1.05 to about 1.5. In another embodiment, the antimicrobial composition comprises at least 0.1 weight percent of polytrimethylene ether glycol. In another embodiment, the antimicrobial composition comprises at least 0.1 weight percent of trimethylene glycol dimer. In another embodiment, the antimicrobial composition comprises a blend of two trimethylene glycol oligomers or a blend of one or more trimethylene glycol oligomers with trimethylene glycol dimer.

Another embodiment is a method for killing, inhibiting, or preventing the growth of at least one microbe in a composition, the method comprising adding to the composition one or more of a trimethylene glycol oligomer of the formula $R(CH_2CH_2CH_2-O-CH_2CH_2CH_2)_nR^1$ wherein R and $R^1$ are hydroxyl, amine, or ester functionalities, and n is 2 or higher. In one embodiment R and $R^1$ are hydroxyl. The method can provide a reduction in antimicrobial activity of greater than 2, or greater than 3, or greater than 5, or greater than 7 $\log_{10}$ against *Escherichia coli* or *Staphylococcus*

*aureus* after 24 hours, as compared to compositions without one or more of a trimethylene glycol. oligomer.

In one embodiment, the method comprises adding to the composition at least 50 weight percent, 30 weight percent, 10 weight percent, 5 weight percent, 1 weight percent, or 0.5 weight percent of the polytrimethylene ether glycol with an average molecular weight of about 650, about 250, less than about 250, or less than about 150. In one embodiment, the method comprises adding to the composition at least 10 weight percent of the polytrimethylene ether glycol with an average molecular weight of less than 650, or ranging from about 250 to about 650, and a polydispersity ranging from about 1.05 to about 1.5. In another embodiment, the method comprises adding to the composition at least 0.1 weight percent of trimethylene glycol oligomer. In another embodiment, the method comprises adding to the composition at least 0.1 weight percent of trimethylene glycol dimer. In another embodiment, the method comprises adding to the composition a blend of two trimethylene glycol oligomers or a blend of one or more trimethylene glycol oligomers with trimethylene glycol dimer. In one embodiment, the composition is a personal care or cosmetic composition.

The molecular weight of the trimethylene ether glycol oligomer can be less than about 650, less than about 500, less than about 300, less than about 250, or less than about 200.

The molecular weight of the trimethylene glycol oligomer can be less than about 650, less than about 500, less than about 300, less than about 250, or less than about 200.

In one embodiment, the antimicrobial composition comprises at least 50 weight percent, 30 weight percent, 10 weight percent, 5 weight percent, 1 weight percent, or 0.5 weight percent of the polytrimethylene ether glycol, based on the total weight of the composition. The polytrimethylene ether glycol preferably has an average molecular weight of about 650, about 250, less than about 250, or less than about 150. In some embodiments, the polytrimethylene ether glycol comprises a mixture of dimer, trimer and tetramer (oligomers) and trimethylene glycol monomer.

The antimicrobial composition is effective against a broad spectrum of microbes, including yeasts, molds, algaes, Gram-positive bacteria such as *Streptococcus, Micrococcus, Clostridia, Listeri, Staphylococcus* (such as *Staphylococcus aureus*), and Gram-negative bacteria such as *Salmonella, Shigella, Pseudomonas, Moraxella, Helicobacter*, acetic acid bacteria, *Legionella, Neisseria, Hemophilus, Klebsiella, Enterobacter, Escherichia* (such as *Escherichia coli*). In one embodiment the antimicrobial composition is effective against Gram-negative and Gram-positive bacteria. In another embodiment the antimicrobial composition is effective against Gram-negative bacteria. The composition can exhibit a reduction in antimicrobial activity of greater than 2, or greater than 3, or greater than 5, or greater than 7 $\log_{10}$ against *Escherichia coli* or *Staphylococcus aureus* after 24 hours as compared to compositions without the trimethylene glycol oligomers disclosed herein.

The compositions disclosed herein can be used as alternatives to conventional antimicrobial agents or can be combined with other conventional and non-conventional antimicrobial agents to enhance their activities.

Trimethylene glycol oligomers, such as the dimer, can be prepared by any known method in the literature starting from 1,3-propanediol. The dimer is a by-product in the 1,3-propanediol manufacturing process, and can be isolated. The oligomers, including dimer, can also be obtained from low molecular weight polytrimethylene glycol using techniques such as fractional distillation or short path distillation. In one embodiment the trimethylene glycol oligomer is formed from biologically-derived 1,3-propanediol.

Trimethylene glycol oligomers, also known as polytrimethylene glycol, are oligomers in which at least 50% of the repeating units are trimethylene ether units. Copolymers of trimethylene glycol comprise at least 50% trimethylene ether repeating units, more typically from about 75% to 99.9%, still more typically from about 90% to 99.9%, and even more typically from about 99% to 99.9%.

The trimethylene glycol oligomers are preferably prepared by polycondensation of monomers comprising 1,3-propanediol (trimethylene glycol), thus resulting in oligomers or co-oligomers containing —($CH_2CH_2CH_2O$)— linkages (trimethylene ether repeating units). As indicated above, at least 50% of the repeating units are trimethylene ether units.

In addition to the trimethylene ether units, lesser amounts of other units, such as other polyalkylene ether repeating units, may be present. In the context of this disclosure, the term "trimethylene glycol oligomer" encompasses trimethylene glycol oligomers made from substantially pure 1,3-propanediol, as well as those oligomers (including those disclosed below) containing up to about 50% by weight of comonomers. By "substantially pure" is meant a purity of greater than about 99%, and more preferably greater than about 99.9%

The 1,3-propanediol monomer employed for preparing the polytrimethylene glycol can be obtained by any of the various well known chemical routes or by biochemical transformation routes. In one embodiment, the 1,3-propanediol is obtained biochemically from a renewable source ("biologically-derived" 1,3-propanediol).

A highly preferred source of 1,3-propanediol is via a fermentation process using a renewable biological source. As an illustrative example of a starting material from a renewable source, biochemical routes to 1,3-propanediol (PDO) have been disclosed that utilize feedstocks produced from biological and renewable resources such as corn feed stock. For example, bacterial strains able to convert glycerol into 1,3-propanediol are found in the species *Klebsiella, Citrobacter, Clostridium*, and *Lactobacillus*. The technique is disclosed in several patents, including U.S. Pat. No. 5,633,362, U.S. Pat. Nos. 5,686,276 and 5,821,092. For example, U.S. Pat. No. 5,821,092 discloses a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, such processes can provide a rapid, inexpensive and/or environmentally responsible source of 1,3-propanediol monomer.

The biologically-derived 1,3-propanediol, such as produced by the processes disclosed and referenced above, contains carbon from the atmospheric carbon dioxide incorporated by plants, which compose the feedstock for the production of the 1,3-propanediol. Thus, in some embodiments, the biologically-derived 1,3-propanediol for use in the compositions disclosed herein contains only renewable carbon, and not fossil fuel-based or petroleum-based carbon. In some embodiments, a combination of 1,3-propanediol from renewable sources and from fossil-fuel/petroleum-based carbon can be used. The trimethylene glycol oligomer and antimicrobial compositions utilizing the biologically-derived 1,3-propanediol, therefore, may have less impact on the environment as the 1,3-propanediol used in the compositions does not deplete diminishing fossil fuels and, upon degradation, releases carbon back to the atmosphere for use by plants once again. Thus, in some embodiments, the compositions disclosed herein can be characterized as more natural and having less environmental impact than similar compositions comprising petroleum based glycols.

The biologically-derived trimethylene glycol oligomer and polymer can be distinguished from similar compounds produced from a petrochemical source or from fossil fuel carbon by dual carbon-isotopic finger printing. This method usefully distinguishes chemically-identical materials, and apportions carbon in the copolymer by source (and possibly year) of growth of the biospheric (plant) component. The isotopes, $^{14}C$ and $^{13}C$, bring complementary information to this problem. The radiocarbon dating isotope ($^{14}C$), with its nuclear half life of 5730 years, clearly allows one to apportion specimen carbon between fossil ("dead") and biospheric ("alive") feedstocks (Currie, L. A. "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc) (1992) 3-74). The basic assumption in radiocarbon dating is that the constancy of $^{14}C$ concentration in the atmosphere leads to the constancy of $^{14}C$ in living organisms. When dealing with an isolated sample, the age of a sample can be deduced approximately by the relationship $$t=(-5730/0.693)\ln(A/A_0)$$

where t=age, 5730 years is the half-life of radiocarbon, and A and $A_0$ are the specific $^{14}C$ activity of the sample and of the modern standard, respectively (Hsieh, Y., *Soil Sci. Soc. Am J.*, 56, 460, (1992)). However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of ca. $1.2\times10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M \approx 1.1$.

The stable carbon isotope ratio ($^{13}C/^{12}C$) provides a complementary route to source discrimination and apportionment. The $^{13}C/^{12}C$ ratio in a given biosourced material is a consequence of the $^{13}C/^{12}C$ ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway. Within the precision of measurement, $^{13}C$ shows large variations due to isotopic fractionation effects, the most significant of which for the present disclosure is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "$C_3$" (or Calvin-Benson) photosynthetic cycle and those that incorporate the "$C_4$" (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphoenol-pyruvate carboxylase, is the primary carboxylation reaction. The first stable carbon compound is a 4-carbon acid, which is subsequently decarboxylated. The $CO_2$ thus released is refixed by the $C_3$ cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) (Weber et al., *J. Agric. Food Chem.*, 45, 2942 (1997)). Coal and petroleum fall generally in this latter range. The $^{13}C$ measurement scale was originally defined by a zero set by pee dee belemnite (PDB) limestone, where values are given in parts per thousand deviations from this material. The "$\delta^{13}C$" values are in parts per thousand (per mil), abbreviated ‰, and are calculated as follows:

$$\delta^{13}C \equiv \frac{(^{13}C/^{12}C)\ \text{sample} - (^{13}C/^{12}C)\ \text{standard}}{(^{13}C/^{12}C)\ \text{standard}} \times 1000‰$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

Biologically-derived 1,3-propanediol, and compositions comprising biologically-derived 1,3-propanediol, therefore, can be completely distinguished from their petrochemical derived counterparts on the basis of $^{14}C$ ($f_M$) and dual carbon-isotopic fingerprinting, indicating new compositions of matter. The ability to distinguish these products is beneficial in tracking materials in commerce. For example, products comprising both "new" and "old" carbon isotope profiles can be distinguished from products made only of "old" materials. Hence, such materials can be followed in commerce on the basis of their unique profile and for the purposes of defining competition, for determining shelf life, and especially for assessing environmental impact.

Preferably the 1,3-propanediol used as a reactant in preparing polytrimethylene glycol, or as a component of the reactant, has a purity of greater than about 99%, and more preferably greater than about 99.9% by weight as determined by gas chromatographic analysis. Particularly preferred are the purified 1,3-propanediols as disclosed in US20040260125A1, US20040225161A1 and US20050069997A1, and trimethylene glycol oligomer made therefrom as disclosed in US20050020805A1.

The purified 1,3-propanediol preferably has the following characteristics:

(1) an ultraviolet absorption at 220 nm of less than about 0.200, and at 250 nm of less than about 0.075, and at 275 nm of less than about 0.075; and/or (2) a L*a*b*"b*" color value of less than about 0.15 (ASTM D6290), and an absorbance at 270 nm of less than about 0.075; and/or (3) a peroxide composition of less than about 10 ppm; and/or (4) a concentration of total organic impurities (organic compounds other than 1,3-propanediol) of less than about 400 ppm, more preferably less than about 300 ppm, and still more preferably less than about 150 ppm, as measured by gas chromatography.

Trimethylene glycol oligomer can be made via a number of processes known in the art, such as disclosed in U.S. Pat. Nos. 6,977,291 and 6,720,459.

As indicated above, polytrimethylene ether glycol may contain lesser amounts of other polyalkylene ether repeating units in addition to the trimethylene ether units. The monomers for use in preparing trimethylene glycol oligomer can, therefore, contain up to 50% by weight (preferably about 20 wt % or less, more preferably about 10 wt % or less, and still more preferably about 2 wt % or less), of comonomer diols in addition to the 1,3-propanediol reactant. Comonomer diols that are suitable for use in the process include aliphatic diols, for example, ethylene glycol, 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4,4,5,5-octafluoro-1,6-hexanediol, and 3,3,4,4,5,5,6,6,7,7,8,8,9,9,10,10-hexadecafluoro-1,12-dodecanediol; cycloaliphatic diols, for example, 1,4-cyclohexanediol, 1,4-cyclohexanedimethanol and isosorbide; and polyhydroxy compounds, for example, glycerol, trimethylolpropane, and pentaerythritol. A preferred group of comonomer diols is selected from the group consisting of ethylene glycol, 2-methyl-1,3-propanediol, 2,2-dimethyl-1,3-propanediol, 2,2-diethyl-1,3-propanediol, 2-ethyl-2-(hydroxymethyl)-1,3-propanediol, C6-C10 diols (such as 1,6-hexanediol, 1,8-octanediol and 1,10-decanediol) and isosorbide, and mixtures thereof. A particularly preferred diol other than 1,3-propanediol is ethylene glycol, and $C_6$-$C_{10}$ diols can be particularly useful as well.

One preferred polytrimethylene glycol containing comonomer is poly(trimethylene-ethylene ether)glycol such as disclosed in US2004/0030095A1. Preferred poly(trimethylene-co-ethylene ether)glycols are prepared by acid catalyzed polycondensation of from 50 to about 99 mole % 1,3-propanediol, preferably from about 60 to about 98 mole %, and more preferably from about 70 to about 98 mole %; and up to 50 to about 1 mole % ethylene glycol, preferably from about 40 to about 2 mole %, and more preferably from about 30 to about 2 mole %.

Polytrimethylene glycol useful in the compositions and methods disclosed herein can contain small amounts of other repeat units, for example, from aliphatic or aromatic diacids or diesters, such as disclosed in U.S. Pat. No. 6,608,168. This type of trimethylene glycol oligomer can also be called a "random polytrimethylene ether ester", and can be prepared by polycondensation of 1,3-propanediol reactant and about 10 to about 0.1 mole % of aliphatic or aromatic diacid or esters thereof, such as terephthalic acid, isophthalic acid, bibenzoic acid, naphthalic acid, bis(p-carboxyphenyl)methane, 1,5-naphthalene dicarboxylic acid, 2,6-naphthalene dicarboxylic acid, 2,7-naphthalene dicarboxylic acid, 4,4'-sulfonyl dibenzoic acid, p-(hydroxyethoxy)benzoic acid, and combinations thereof, and dimethyl terephthalate, bibenzoate, isophthlate, naphthalate and phthalate; and combinations thereof. Of these, terephthalic acid, dimethyl terephthalate and dimethyl isophthalate are preferred.

Polytrimethylene ether polymers with end groups other than hydroxyl end groups can also be used. For example, polytrimethylene glycol oligomers with amine and ester end groups are disclosed in U.S. Patent Applications 2008/0108845 and Ser. No. 12/704,867.

In one embodiment, the antimicrobial composition further comprises one or more additional antimicrobial additives. The additional antimicrobial additives can be any known in the art, and in combination with the trimethylene glycol oligomers disclosed herein may have an synergistically intensified microbial effect.

Antimicrobial agents are well known in the art, and are disclosed in Kirk-Othmer Encyclopedia of Chemical Technology, Industrial Antimicrobial Agents, Thomas McEntee, 2000, John Wiley & Sons, Inc., DOI: 10.1002/0471238961.0914042113030514.a01.

Suitable antimicrobial agents include: quaternary amines such as benzalkonium chlorides, dialkyldimethyl-ammonium chlorides, cetyltrimethyl-ammonium bromide, cetylpyridinium chloride, 3-(trimethoxysilyl)-propyldimethyl-octadecyl-ammonium chloride, phenolics, 2-benzyl-4-chlorophenol, o-phenylphenol, sodium o-phenylphenate, pentachlorophenol, 2(2',4'-dichlorophenoxy)-5-chlorophenol, Irgasan®, and 4-chloro-3-methyl phenol; organo halogen compounds such as p-tolydiiodomethyl sulfone, 3-iodo-2-propynylbutyl carbamate, trichloroisocyanurate, sodium dichloroisocyanurate, potassium dichloroisocyanurate, monotrichloroisocyanurate, potassium dichloroisocyanurate, 1:4 dichlorodimethylhydantoin, bromochlorodimethylhydantoin, 2,2'-dibromo-3-nitrilopropionamide, bis(1,4-bromoacetoxy)-2-butene, 1,2-dibromo-2,4-dicyanobutane, 2-bromo-2-nitropropane-1,3-diol, and benzyl bromoacetate; organometallics such as 10,10'-oxybisphenoxi-arsine, tributyltin oxide, tributyltin fluoride, copper 8-quinolinolate, copper naphthenate, chromated copper arsenate, ammoniacal copper arsenate, cuprous oxide, 10,10'-oxybisphenoxarsine, copper quinolinolate copper oleate, copper ethylenediamine tetraacetate, barium metaborate, and copper carbamates; organosulfur compounds such as methylenebisthiocyanate, methylenebisthiocyanate, vinylenebisthiocyanate, chloroethylenebisthiio-cyanate, sodium dimethyldithiocar-bamate, disodium ethylenebisdithiocar-bamate, zinc dimethyldithiocar-bamate, and bis(trichloromethyl) sulfone; heterocyclics such as tetrahydro-3,5-dimethyl-2H-1,3,5-thiadiazine-2-thione (DMTT), sodium pyridinethione, sodium omadine, zinc pyridinethione, 1,2-benzisothiazoline-3-one, 2-(n-octyl)-4-isothiazolin-3-one, 2-(4-thiazolyl)benzimidazole, N-(trichloromethylthio)-4-cyclohexene-1,2-dicarboximide, N-(trichloromethylthio)-phthalimide, 5-chloro-2-methyl-4-isothiazolin-3-one 2-methyl-4-isothiazolin-3-one; other nitrogen compounds such as N-cocotrimethylenediamine, N-[alpha-(1-nitroethyl)benzyl]-ethylenediamine, 2-(hydroxymethyl)amino-ethanol, 2-(hydroxymethyl)amino-2-methylpropanol, 2-hydroxymethyl-2-nitro-1,3-propanediol, hexahydro-1,3,5-tris-(2-hydroxyethyl)-σ-triazine, hexahydro-1,3,5-triethyl-σ-triazine, 4-(2-nitrobutyl)morpholine, 4,4'-(2-ethyl-2-nitro-trimethylene)-dimorpholine, glutaraldehyde, 1,3-dimethylol-5,5-dimethyl-hydantoin, and imidazolidinyl urea; alkanediols such as 1,2-pentanediol, 1,2-hexanediol, 1,2-octanediol, 1,2-decanediol; and miscellaneous classes such as nitromethane, acrolein, mixed dioxaborinanes, 2,6-dimethyl, 1,3-dioxanol-4 acetate, 1-(3-chloroallyl)-3,5,7-triaza-1-azoniaadamantane chloride, 2-chloro-N-

(hydroxymethyl)acetamide, β-bromo-β-nitrostyrene, methyl-3,5,7-triaz-1-azoniatricyclodecane chloride, 1-(hydroxymethyl)5,5-dimethyl hydantoin, 2-bromo-2-nitropropanediol, methanol, [[2-(dihydro-5-methyl-3(2H)-oxazolyl)-1-methylethoxy]ethoxy]methoxyl, dimethyl benzyl tdichloro-isothiozal-3-one, decylthioethylamine, decylthioethylamine-hydrochloride, N-hydroxymethyl-3,5-dimethylpyrazole, phospholipids, benzoic/sorbic acids, and natural materials and essential oils.

The antimicrobial compositions disclosed herein can be used in any application in which antimicrobial activity is desired. The trimethylene glycol oligomer and polymer can provide reduced environmental footprints and 100% renewably sourced ingredient (i.e., petroleum free). They are available in a wide polarity range from hydrophilic to lipophilic due to varied chain length. Examples of applications for which the compositions are useful include: metalworking fluid, paint, paper, plastic, textile, wood, cleaning and disinfectant solutions, coatings and paints, seed coatings, inkjet inks, transformer fluids, crop protection application, pesticides, fungicides, food applications, house hold products, home cleaning products, coatings for paperboard packaging, car care products, laundry additives, aqueous mineral slurries, paper coating compositions, and adhesives.

In one embodiment, the antimicrobial composition is a personal care or cosmetic composition. Examples of suitable personal care or cosmetic compositions include skin care products, cosmetics, (including liquid or powder foundation, liquid or solid eyeliner, mascara, cream eye shadow, tinted powder, "pancake" type powder to be used dry or moistened, etc.), perfumes, deodorants, insect repellants, anesthetics, medicinal agents, mouthwashes, shampoos, hair conditioners, sun care products, soaps, hair anti-dandruff compositions, hair growth promoter compositions, hair colorant compositions, hair bleaching compositions, hair anti-frizzing compositions, hair relaxer compositions, cleansing wipes, disinfecting wipes, acne treatment products, hand sanitizer, personal lubricants, skin cleaning compositions. body lotion, hand cream, topical cream, aftershave lotion, skin toner, mouth wash, toothpaste, sunscreen lotion, and baby products such as, but not limited to, cleansing wipes, baby shampoo, baby soap, and diaper cream. deodorant, antimicrobial creams. The antimicrobial compositions can also be applied to wound care items, such as, for example, wound healing ointments, wound coverings, bandages, tape, and steri-strips, and medical articles such as medical gowns, caps, face masks, shoe-covers, and surgical drops. The trimethylene glycol oligomer or polymers can have additional functions in addition to antimicrobial activity, such as moisturizer, humectant, viscosity enhancer, thickener, solvent, diluent, a carrier for another active ingredient, preservative, or emulsifier.

Examples of substances that can suitably be included in the personal care products as active personal care ingredients include the following:

(1) perfumes and fragrances, which give rise to an olfactory response in the form of a fragrance, and deodorant perfumes which, in addition to providing a fragrance response, can also reduce body malodor;
(2) skin coolants, such as menthol, menthyl acetate, menthyl pyrrolidone carboxylate, N-ethyl-p-menthane-3-carboxamide and other derivatives of menthol, which give rise to a tactile response in the form of a cooling sensation on the skin;
(3) emollients, such as isopropylmyristate, silicone oils, mineral oils and vegetable oils, which give rise to a tactile response in the form of an increase in skin lubricity;
(4) deodorants other than perfumes, whose function is to reduce the level of or eliminate micro flora at the skin surface, especially those responsible for the development of body malodor, including precursors of deodorants;
(5) antiperspirant actives, whose function is to reduce or eliminate the appearance of perspiration at the skin surface;
(6) moisturizing agents, that keep the skin moist by either adding moisture or preventing from evaporating from the skin;
(7) cleansing agents, that remove dirt and oil from the skin;
(8) sunscreen active ingredients that protect the skin and hair from UV and other harmful light rays from the sun;
(9) hair treatment agents that condition hair, clean hair, detangle hair, act as styling agents, anti-dandruff agents, hair growth promoters, hair dyes and pigments, hair perfumes, hair relaxers, hair bleaching agents, hair moisturizers, hair oil treatment agents and antifrizzing agents;
(10) oral care agents, that clean, whiten, deodorize and/or protect the teeth and gum;
(11) denture adhesives, that provide adhesion properties to dentures;
(12) beauty aids, such as powders, pigments and colorants; and
(13) medicinal agents.

Further examples of agents for use on skin include abrasives; absorbents; aesthetic components such as opacifying agents and pearlescent aids such as ethylene glycol distearate and $TiO_2$ coated mica; essential oils; skin sensates; cosmetic and drug astringents such as clove oil, menthol, camphor, eucalyptus oil, eugenol, menthyl lactate and witch hazel distillate; anti-acne agents such as resorcinol, sulfur, salicylic acid, benzoyl peroxide, erythromycin and zinc; anti-caking agents; antimicrobial agents such as iodopropyl butylcarbamate; antioxidants; cosmetic biocides; external analgesics; pH modifiers such as citric acid, sodium citrate, succinic acid, phosphoric acid, sodium hydroxide and sodium carbonate; skin bleaching and lightening agents such as hydroquinone, kojic acid, ascorbic acid, magnesium ascorbyl phosphate and ascorbyl glucosamine; skin soothing and/or healing agents such as panthenol and derivatives like ethyl panthenol, aloe vera, pantothenic acid and its derivatives, allantoin; bisabolol and dipotassium glycyrrhizinate; retinoids such as retinol palmitate); tocopheryl nicotinate; skin treating agents; and vitamins and derivatives thereof.

Humectants are agents that control the moisture exchange between the product and air, both in the container and on the skin. Humectants have also been described as compounds that prevent drying of skin or that increase the water content of the top layers of skin (e.g., hygroscopic compounds).

Although polytrimethylene ether glycol is itself a useful humectant that has a strong tendency to retain water and forms gel in the absence of a gelling agent, it can also be used with other humectants or moisturizing agents, that: (a) facilitate hydration of the skin, scalp, hair, or nails by inhibiting or preventing loss of water; (b) absorb water from the atmosphere and hydrate the skin, scalp, hair, or nails; (c) enhance the ability of the skin, scalp, hair, or nails to absorb water directly from the atmosphere; or (d) any combination thereof. Moisturizing agents also minimize or prevent the skin, scalp, hair, or nails from drying and cracking.

Suitable moisturizing agents include hydrophobic agents, hydrophilic agents and combinations thereof. Examples of moisturizing agents are allantoin, glycerol, polyglycerylmethacrylate, panthenol, polyols, ceramide, borage oil (linoleic acid), tocopherol (Vitamin E), tocopherol linoleate, dimethicone, hyaluronic acid, sodium peroxylinecarbolic acid (sodium PCA), wheat protein (e.g., laurdimonium hydroxypropyl hydrolyzed wheat protein), hair keratin amino acids, panthenol; primrose oil; GLA 3 and other fish oils that may include, for example, the omega-3 and omega-6 oils and/or linoleic acid; and flax seed oil, and mixtures thereof. Other moisturizing agents can also be used.

Numerous sunscreen agents are suitable for use in the personal care compositions of the present invention. Examples include, p-aminobenzoic acid, its salts and its derivatives, anthranilates, salicylates, cinnamic acid derivatives, dihydroxy cinnamic acid derivatives, trihydroxy cinnamic acid derivatives, dibenzalacetone, dibenzalacetophenone, naphtholsulfonates, dihydroxynaphtholic acid and its salts, coumarin derivatives, diazoles, quinine salts, quinoline derivatives, hydroxy- and methoxy-substituted benzophenones, uric and vilouric acids, tannic acid and its derivatives, hydroquinone and benzophenones. In accordance with this invention, an effective amount will normally be from about 0.01 to about 10% by weight, preferably from about 0.1 to about 5% by weight, based on the weight of the composition.

Typically, the active ingredient in deodorant-antiperspirant compositions is a basic aluminum compound. Examples of such materials are aluminum chlorhydroxide, basic aluminum bromide, iodide or nitrate, and basic aluminum hydroxy chloride-zirconyl hydroxy oxychloride.

Cleaning agents are typically anionic, cationic, non-ionic or amphoteric surfactants. Typical anionic surfactants are carboxylates, sulfonates, sulfates or phosphates, e.g. fatty acid soaps, salts of lauryl sulfate and salts of lauryl ether sulfate. Examples of cationic surfactants are aliphatic mono, di and polyamines derived from fatty and rosin acids, amine oxides, ethoxylated alkyl amines and imidazolines. Examples of non-ionic surfactants are polyoxyethylene surfactants, alkylphenol ethoxylates, carboxylic acid esters, e.g., mono and diglycerides, polyoxyethylene esters and fatty acid diethanolamine condensates. Amphoteric surfactants are those containing combinations of the anionic and cationic groups described above, particularly those containing both acid carboxyls and basic nitrogen groups. Typical amphoteric surfactants are imidazolines and betaines, e.g., lauric and myristic imidazolines and betaines, and amidopropylbetaines.

A variety of medicinal agents also may be present as active ingredients in the compositions of the invention. Non-limiting examples are anti-acne additives, anti-cellulite agents, antihistamines, anti-inflammatory agents, antimicrobials, spermicides, antiseptics, antifungal agents and antiviral agents, and local anesthetics.

The trimethylene glycol oligomer is generally dissolved, suspended or emulsified into a vehicle. A variety of other ingredients, in addition to those already mentioned, may also be present in the personal care compositions of the present invention. Examples of such other ingredients include gelling agents, surfactants, emulsifiers, and preservatives.

Cellulosic gums also can be used as additives in the compositions of this invention. For instance, US2003/0198616A1 describes a moisturizing skin gel wherein a water-soluble hydroxyalkylcellulose polymer typically performs a dual function of gelling the composition and forming a moisture barrier to reduce transepidermal water loss. Preferred cellulosic gums include water-soluble hydroxyalkylcellulose polymers such as hydroxymethylcellulose, hydroxyethylcellulose and hydroxypropylcellulose. Other thickening agents which have been used in skin-contacting compounds, include acacia, agar, alginate, carrageenan, gum tragacanth, xanthan gum, collagen, carboxypolymethylene, glyceryl monostearate, polyvinylpyrrolidone and polyacrylamide.

Surfactants can also be used in the personal care compositions. Typical surfactants are disclosed in US2003/0007939A1.

Other commonly used ingredients in personal care composition include preservatives, which are known in the art and commercially available. Examples include benzyl alcohol, methyl paraben, propyl paraben, DMDM hydantoin, methylchloroisothiaoline, methylisothiazolinone, imidazolidinyl urea phenoxyethanol, sodium benzoate and benzoic acid. EDTA and salts thereof are often used to further enhance preservation.

Although additives such as those described above can be advantageously included in the compositions without limitation, the total amount of these additives generally ranges up to about 8.0 w %, and preferably up to about 3.0 wt %, based on the weight of the personal care composition.

The personal care compositions can be prepared by use of conventional formulation and mixing techniques. Methods of making several personal care compositions using polytrimethylene ether glycol are described in the examples herein, which are exemplary only and not intended to be limiting.

Personal care compositions or products are generally in the form of creams, solutions, emulsions, foams, gels, lotions, ointments, solids, powders, semi-solids, etc. The compositions, thus, may be made into a wide variety of product types. These include but are not limited to solutions, lotions, emulsions, creams, gels, sticks, sprays, ointments, pastes, foams, mousses, shampoos, cosmetics, and dermal patches, etc. Products employing these compositions include but are not restricted to skin care products, cosmetics, deodorants, antiperspirants, insect repellants, anesthetics, shampoos, hair conditioners, sun care products, shower gels, soaps, hair styling gels, hair anti-dandruff compositions, hair growth promoter compositions, hair colorant compositions, hair bleaching agent compositions, hair anti-frizzing agent compositions, hair relaxer compositions, shaving product compositions, lubricating gel compositions, spermicidal gel compositions, and skin cleaning compositions.

Personal care products generally contain an active ingredient incorporated in a delivery vehicle. The desired effect of a personal care product is achieved either by the personal care active ingredients or by the vehicle itself at the site of application, such as the skin or hair. With the aid of the vehicle, i.e. the vehicle acting as a carrier, the active ingredient is delivered to the application site where the desired effect is to be achieved.

The major types of personal care vehicles most frequently fall into the following categories: (a) solutions; (b) emulsions, both oil-in-water and water-in-oil; and including lotions and creams; (c) suspensions; (d) gels; and (e) solids and semi-solids including stick products. An extensive discussion of personal care and cosmetic vehicles is found in the previously incorporated Handbook of Cosmetic Science and Technology, Second Edition, edited by M Paye, A. O. Barel and H. I. Maibach, pages 99-123 (2005).

EXAMPLES

Herein, the following abbreviations are used:
ATCC American Type Culture Collection.
CFU Colony-forming unit
DI Deionized
*E. coli* Escherichia coli
PDO 1,3-propanediol
*S. aureus* Staphylococcus aureus TSA Tryptic soy agar
DPG 1,2-dipropaneglycol
TSB Tryptic soy broth
MW Molecular weight Preparation of Polytrimethylene Glycol Having Number Average Molecular Weight 250:

12 kg of renewably sourced PDO monomer was added to a 20 L glass reactor equipped with a condenser and an agitator, purged with $N_2$ at the rate 3 L/min. 0.1 wt. % of triflic acid (trifluoromethanesulfonic acid) was added into the reactor and the mixture was heated up to 180° C. with agitation set to 200 RPM to allow the acid-catalyzed polycondensation to proceed. The reaction volatiles were condensed in the condenser and the crude polymer product was retained in the reactor. Crude polymer samples were taken periodically for color and molecular weight analysis. Once the desired Mn was achieved, the polymerization was terminated by turning the heat down. An antioxidant, BHT (about 200 ppm) was added to the crude polymer and neutralization was conducted by treating the crude polymer with XUS ion exchange resin in 2 stages. The first stage, the crude polymer was mixed with about 2 wt. % of the ion exchange resin at a temperature of about 105° C. for about 1 hour. In the second stage, an additional 2 wt. % of the ion exchange resin was added to the crude polymer and further mixed for additional 3 hours. Neutralization was conducted under sub-surface nitrogen sparging of 5 L/min and a mixing of 200 RPM. The product was filtered to remove the ion exchange resin. Filtration occurred at 60° C. Once the product was free of solids, it was dried by heating it to about 95° C., with sub-surface nitrogen sparging of about 10 L/min and mixing of 150 RPM.

Fractionation of Polytrimethylene Glycol:

To a 500 mL, 3-neck round bottom flask equipped with a mechanical stirrer, a distillation adapter, a condenser and a graduated distillation receiver, was added 367.6 g of polytrimethylene glycol having number average molecular weight of 250. The polymer was heated with a PID controller connected to a heating mantle and thermocouple. The controller was set to maintain a batch temperature of 50° C. at a power setting of 50% (300 mL-2 L). The flask was fully evacuated, <5 torr, the controller was turned on and the reaction was stirred at 200 rpm. The temperature set point and the stirring speed were increased to a maximum of 280° C. and 300 rpm, respectively as the distillation progressed. Several fractions were collected, approximately every 20 mL, using the distilling receiver to remove the flask containing the fraction while maintaining the vacuum on the distillation pot. The temperature controller and vacuum pump were turned off after 8 hours and the remaining material was allowed to cool overnight under a blanket of nitrogen.

The fractions were analyzed by GC-MS and the different concentration of oligomers present in unfractionated sample and distilled fractions are reported in Table 1.

Trimethylene glycol dimer or di(1,3-propanediol) used was a by-product isolated from the manufacturing process of 1,3-propanediol from acrolein.

TABLE 1

|      | PDO   | Dimer | Trimer | Tetramer | Pentamer | Heamer | Heptamer |
|------|-------|-------|--------|----------|----------|--------|----------|
| Unfractionated | 2.7%  | 15.0% | 20.0%  | 22.4%    | 18.6%    | 15.9%  | 3.8%     |
| B-1  | 32.9% | 46.5% | 12.7%  | 0.9%     | —        | —      | —        |
| B-2  | 16.6% | 52.0% | 21.8%  | 5.0%     | —        | —      | —        |
| B-3  | 4.9%  | 52.4% | 31.4%  | 8.7%     | 0.6%     | —      | —        |
| B-4  | 1.7%  | 43.4% | 36.4%  | 15.6%    | 1.1%     | —      | —        |
| B-5  | 0.5%  | 37.4% | 40.4%  | 18.4%    | 1.8%     | —      | —        |
| B-6  | —     | 27.9% | 44.1%  | 23.4%    | 3.2%     | —      | —        |
| B-7  | —     | 17.2% | 44.0%  | 30.9%    | 6.7%     | —      | —        |
| B-8  | —     | 9.7%  | 42.8%  | 36.5%    | 9.7%     | —      | —        |
| B-9  | —     | 2.0%  | 41.8%  | 42.0%    | 12.8%    | —      | —        |
| B-10 | —     | —     | 30.5%  | 46.0%    | 19.8%    | 2.3%   | —        |
| B-11 | —     | —     | 18.9%  | 48.1%    | 26.9%    | 5.3%   | —        |
| B-12 | —     | —     | 10.6%  | 49.5%    | 32.3%    | 7.0%   | —        |
| B-13 | —     | —     | 3.9%   | 47.7%    | 38.5%    | 9.4%   | —        |
| B-14 | —     | —     | 0.6%   | 41.6%    | 45.0%    | 12.2%  | —        |
| B-15 | —     | —     | —      | 28.7%    | 49.7%    | 20.4%  | 0.7%     |
| B-16 | —     | —     | —      | 17.0%    | 51.4%    | 27.6%  | 2.0%     |

Bacterial Cultures:

Two test microorganisms were used, the Gram-negative bacterium, *Escherichia coli* ATCC 8739, and the Gram-positive bacterium, *Staphylococcus aureus* ATCC 6538. These microrganisms were grown overnight in 10 mL Tryptic soy broth (TSB) starter cultures, and then inoculated into Klett flasks containing 30 mL of TSB. The Klett flasks were incubated on an incubator shaker at 37° C. until the desired Klett reading was obtained (early stationary phase). Each test inoculum was prepared by adding 0.1 mL of the Klett flask culture to 9.9 mL of Mueller-Hinton II Broth (cation-adjusted) or M9 Broth.

Preparation of M9 Broth:

Five separate solutions were prepared containing the following ingredients and each solution was filter sterilized with 0.2 micron filter:

Solution 1: 990 mL of DI water, 6 g $Na_2HPO_4$, 3 g $KH_2PO_4$, 0.5 g NaCl, and 1 g $NH_4Cl$.

Solution 2: 20 g of glucose (dextrose) in DI water to a final volume of 100 mL

Solution 3: 24.65 g of $MgSO_4 \times 7H_2O$ in DI water to a final volume of 100 mL Solution 4: 1.47 g of $CaCl_2$ in DI water to a final volume of 100 mL Solution 5: 10 g of yeast extract in DI water to a final volume of 100 mL The final broth was prepared by mixing 99 mL of solution 1, 1 mL of solution 2, 0.1 mL of solution 3, 0.1 mL of solution 4, 0.2 mL of solution 5 and 900 mL of DI water and adjusting the pH to 7.2.

Example 1

Antibacterial Properties of Poly(Trimethylene Ether)Glycol

Samples of polytrimethylene ether glycol with an average molecular weight of 250 and 650 (Cerenol® 650, available from E. I. du Pont de Nemours and Company, Wilmington, Del.) were added to Mueller-Hinton II Broth (cation-adjusted) so that the final concentration of the polymer was 30% (1.5 mL polymer+3.5 mL broth) and 50% (2.5 mL polymer+ 2.5 mL broth). The controls were prepared the same way using sterile DI water in place of polymer. The *E. coli* inoculum was added to one set of tubes, the *S. aureus* inoculum was added to another set of tubes. The initial inoculum concentrations were $3.0\times10^5$ CFU/mL and $3.1\times10^5$ CFU/mL for *E. coli* and *S. aureus*, respectively. The tubes were incubated on an incubator-shaker (275 rpm, 37° C.) for approx. 20 h.

Figure 1A:
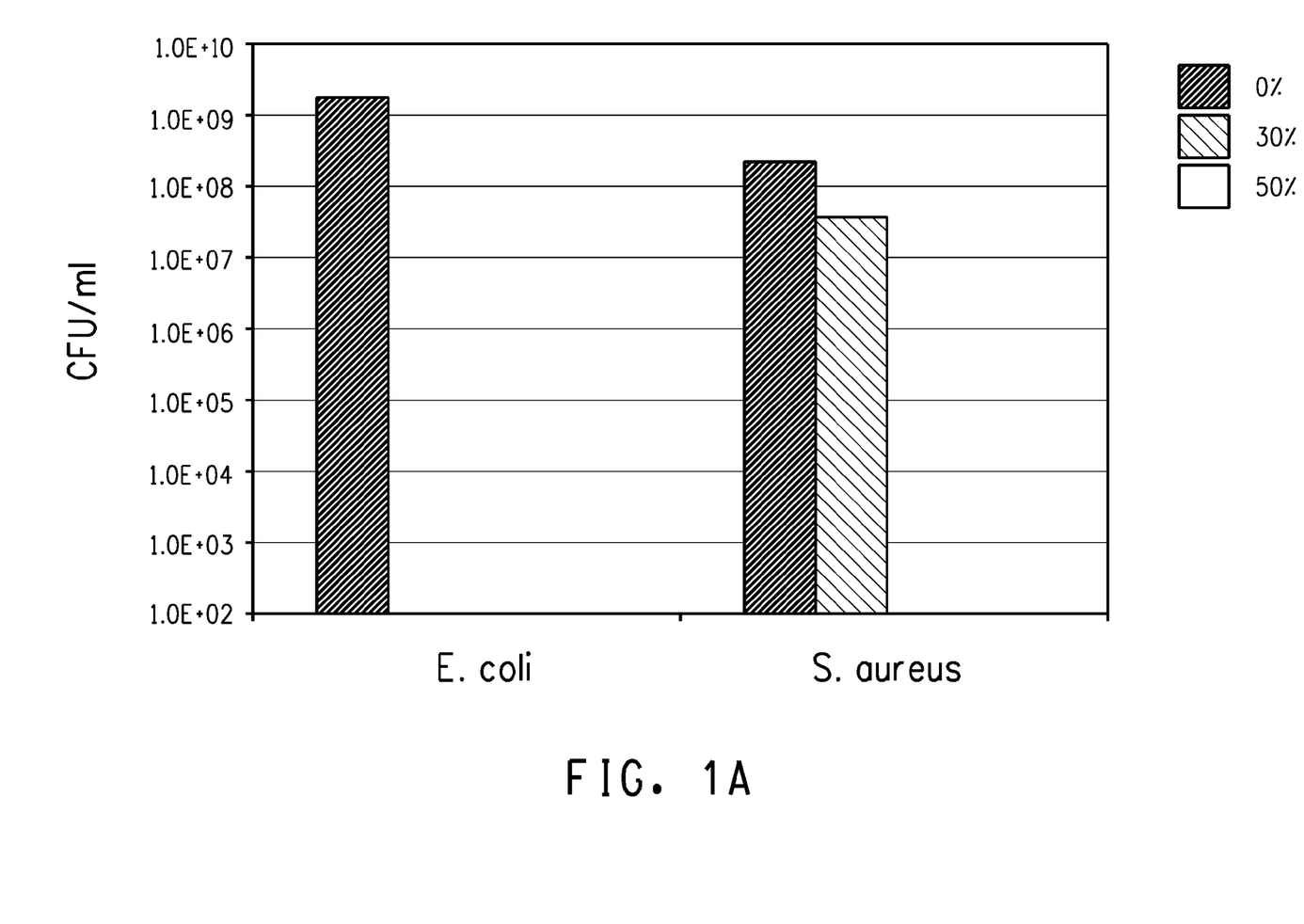
FIG. 1 is a chart showing the efficacy of polytrimethylene glycol having a number average molecular weight (Mn) 250 and 650 at concentrations of 30 and 50% against *E. coli* and *S. aureus*.
Figure 1B:
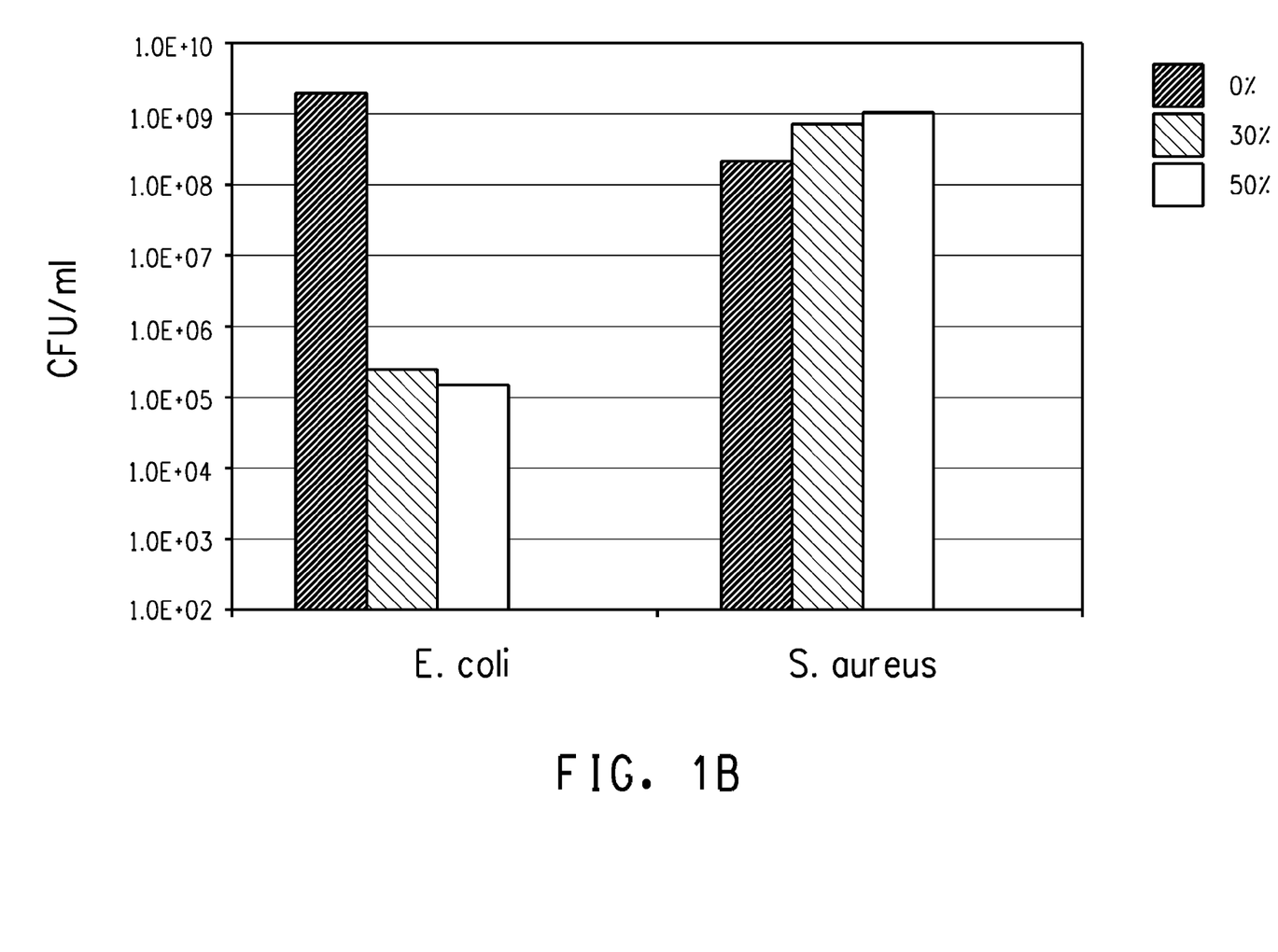

After the incubation, an aliquot from each sample was removed and diluted in sterile phosphate buffer. Each dilution ($10^{-1}$, $10^{-3}$, $10^{-5}$ and $10^{-7}$) was spread plated onto Tryptic soy agar (TSA) plates. The TSA plates were then incubated for approx. 24 h at 37° C., and counted. The results are shown in Table 2. At these concentrations the 250 MW sample was bacteriacidal to *E. coli* as the concentration of cells dropped below the detection limit of 100 CFU/mL. This is a >3-log reduction in cell counts compared to the starting inoculum ($3.0\times10^5$ CFU/mL). At 50%, the 250 MW was also bacteriacidal against *S. aureus*. However, at 30%, it appeared to be only slightly inhibitory. The 650 MW sample was bacteriastatic to *E. coli* at concentrations of 30% and 50% as the concentration of cells after 20 h was approximately the same as the starting concentration. However, the 650 MW sample appeared to have no effect on *S. aureus* as the concentration of cells after 20 h not only exceeded the starting the concentration but also exceeded the concentration in the control. The results are shown graphically in FIG. 1. Numbers in exponential format are indicated with "E", i.e. $2.2\times10^{+9}$ are written as 2.2E+09.

TABLE 2

| Polymer | Inoculum | Polymer Concentration | | |
|---|---|---|---|---|
| | | 0% | 30% | 50% |
| H250 | *E. coli* | 1.9E+09 | <100 | <100 |
| H250 | *S. aureus* | 2.49E+09 | $3.7\times10^7$ | <100 |
| H650 | *E. coli* | 1.9E+09 | $2.4\times10^5$ | $1.5\times10^5$ |
| H650 | *S. aureus* | 2.4E+09 | $8.0\times10^8$ | $1.0\times10^9$ |

Example 2

Antibacterial Properties of Trimethylene Glycol Oligomers

The unfractionated polymer 250 MW, each distilled fraction, and a control were tested for antibacterial or bacteristatic properties against *E. coli*.

Each sample (0.5 ml), or a dilution of the sample (0.5 ml), was added to 4.5 ml of M9 Broth (cation-adjusted) so that the final concentration of the test material was at 1 and 10%. Numbers in exponential format are indicated with "E", i.e. $2.2\times10^{+9}$ are written as 2.2E+09.

Figure 2:
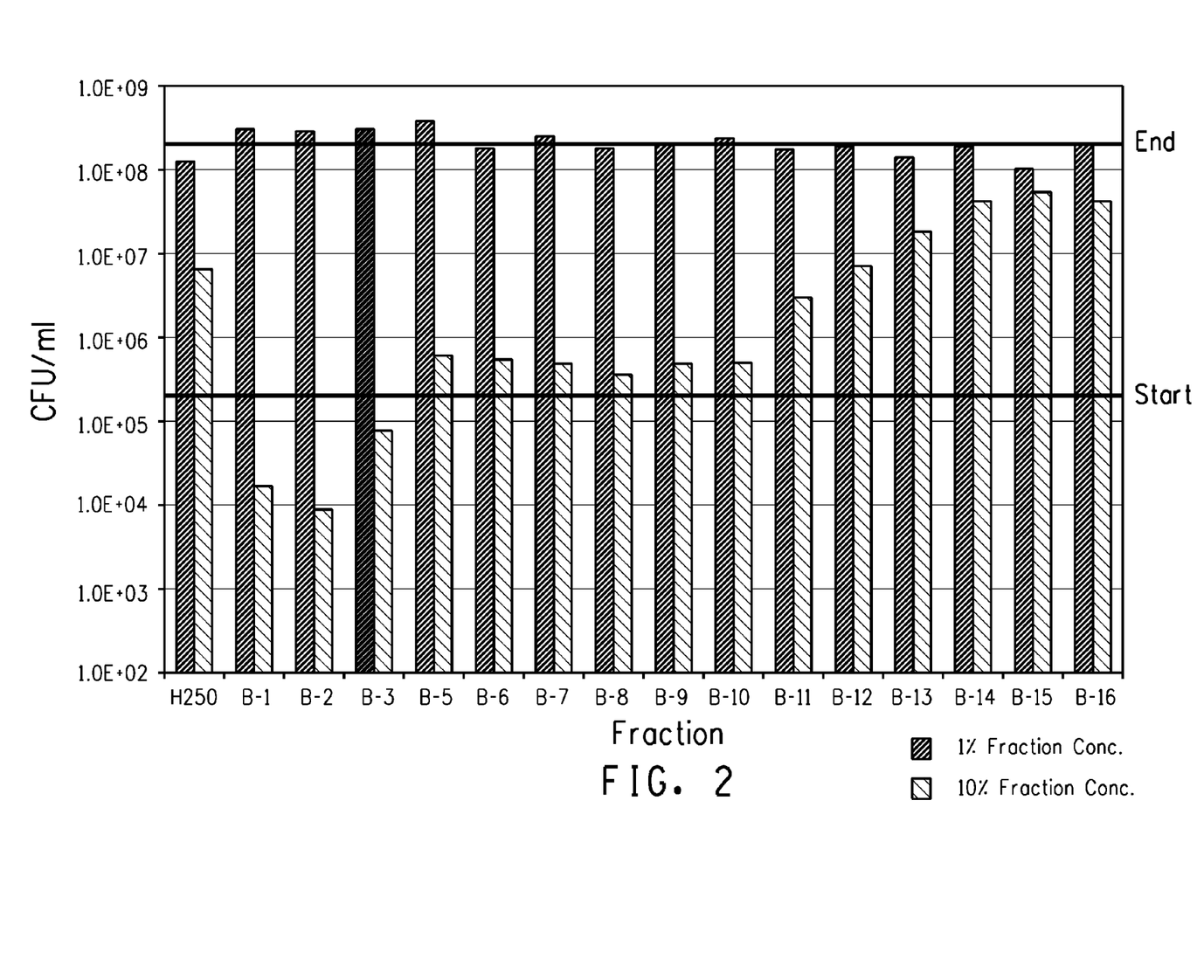
FIG. 2 is a chart showing the efficacy of various volatile trimethylene glycol oligomer fractions obtained from polytrimethylene glycol having a number average molecular weight of 250 at a concentration of 1% or 10% against *E. coli*.

The results are shown below in tabular form below in Table 3. FIG. 2 shows the concentration of *E. coli* with various fractions at a conc. of 1% or 10%. The two black bars indicate the conc. of *E. coli* in the control samples at the start and end of the incubation. They demonstrate that fractions B-1, B-2, and B-3 show bacteristatic effects at 10% concentration.

TABLE 3

| | Results | | |
|---|---|---|---|
| Tube # | Sample | Conc. (%) | CFU/mL |
| 1 | Control-1 | | 2.5E+08 |
| 2 | Unfractionated | 10 | 6.4E+06 |
| 3 | Unfractionated | 1 | 1.3E+08 |
| 4 | Fraction B-1 | 10 | 1.7E+04 |
| 5 | Fraction B-1 | 1 | 2.8E+08 |
| 6 | Fraction B-2 | 10 | 9.0E+03 |
| 7 | Fraction B-2 | 1 | 2.6E+08 |
| 8 | Fraction B-3 | 10 | 7.6E+04 |
| 9 | Fraction B-3 | 1 | 2.8E+08 |
| 10 | Fraction B-4 | 10 | 3.3E+05 |
| 11 | Fraction B-4 | 1 | <10 |
| 12 | Fraction B-5 | 10 | 5.8E+05 |
| 13 | Fraction B-5 | 1 | 3.2E+08 |
| 14 | Fraction B-6 | 10 | 5.4E+05 |
| 15 | Fraction B-6 | 1 | 1.8E+08 |
| 16 | Fraction B-7 | 10 | 4.9E+05 |
| 17 | Fraction B-7 | 1 | 2.6E+08 |
| 18 | Fraction B-8 | 10 | 3.7E+05 |
| 19 | Fraction B-8 | 1 | 1.8E+08 |
| 20 | Fraction B-9 | 10 | 4.8E+05 |
| 21 | Fraction B-9 | 1 | 2.1E+08 |
| 22 | Fraction B-10 | 10 | 4.7E+05 |
| 23 | Fraction B-10 | 1 | 2.4E+08 |
| 24 | Fraction B-11 | 10 | 2.6E+06 |
| 25 | Fraction B-11 | 1 | 1.8E+08 |
| 26 | Fraction B-12 | 10 | 7.2E+06 |
| 27 | Fraction B-12 | 1 | 1.9E+08 |
| 28 | Fraction B-13 | 10 | 1.7E+07 |
| 29 | Fraction B-13 | 1 | 1.4E+08 |
| 30 | Fraction B-14 | 10 | 4.5E+07 |
| 31 | Fraction B-14 | 1 | 1.9E+08 |
| 32 | Fraction B-15 | 10 | 5.4E+07 |
| 33 | Fraction B-15 | 1 | 9.9E+07 |
| 34 | Fraction B-16 | 10 | 4.7E+07 |
| 35 | Fraction B-16 | 1 | 2.1E+08 |
| 36 | Control-2 | | 1.9E+08 |

Example 3

Gram Negative and Gram Positive Antibacterial Properties of Trimethylene Glycol Oligomers The unfractionated mixture, each fraction, and a control were analyzed for antibacterial or bactericidal properties against *S. aureus*. Numbers in exponential format are indicated with "E", i.e. $2.2\times10^{+9}$ are written as 2.2E+09.

Figure 3:
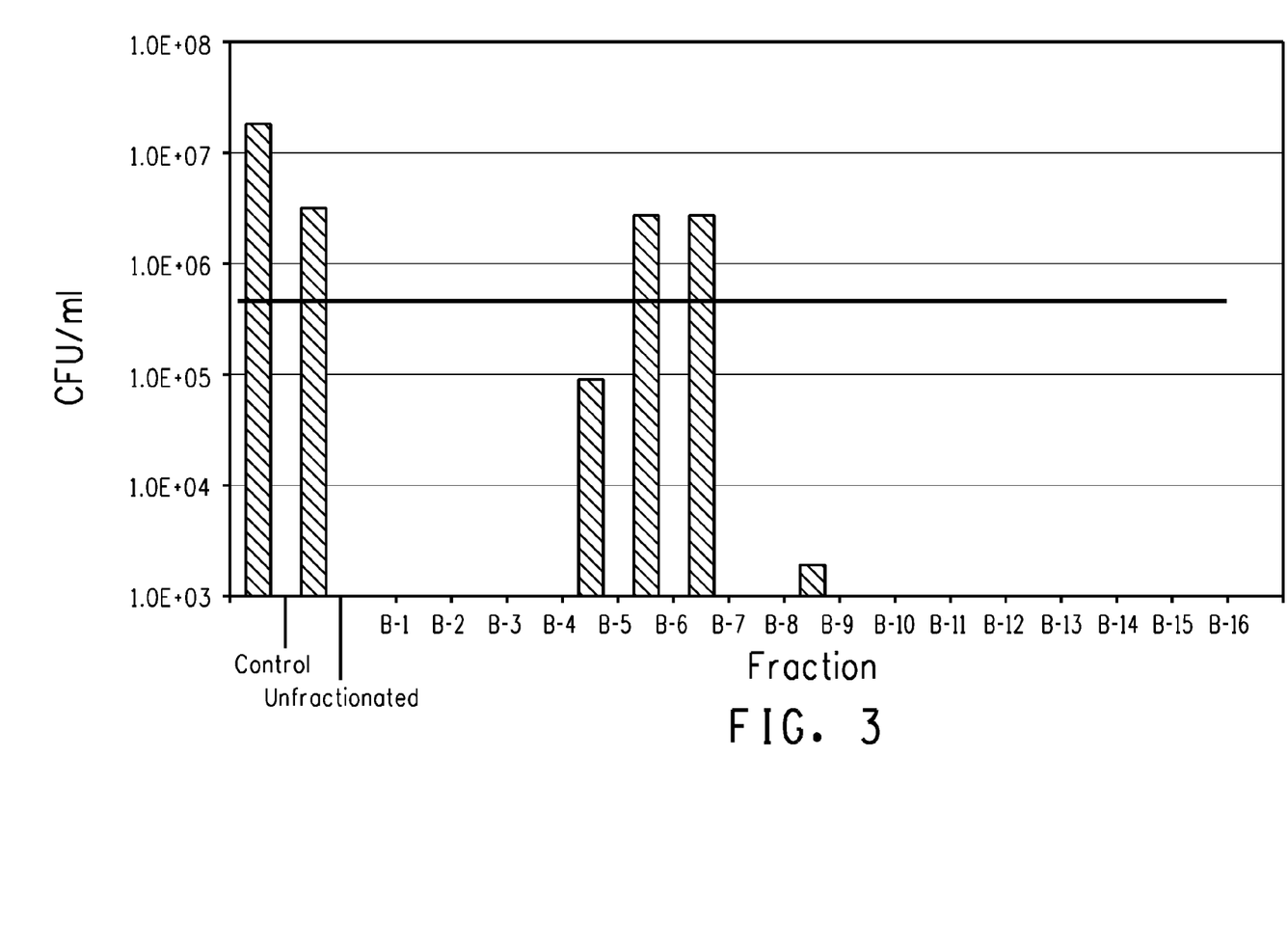
FIG. 3 shows the efficacy of various volatile trimethylene glycol oligomer fractions obtained from polytrimethylene glycol having a number average molecular weight of 250 at a concentration of 10% against *S. aureus*.

The results are shown below in Table 4. FIG. 3 shows the concentration of *S. aureus* with various fractions at a conc. of 10%. The black bar indicates the conc. of *S. aureus* at the start of the incubation. This graph demonstrates that a mixture of PDO oligomers kill or inhibit the growth of Gram-positive bacterium, especially at lower and at higher fractions.

TABLE 4

| Tube # | Sample | Conc. (%) | CFU/mL |
|---|---|---|---|
| 1 | Control-1 | — | 1.5E+07 |
| 2 | Unfractionated | 10 | 3.6E+06 |
| 3 | Fraction B-1 | 10 | <1.0E+03 |
| 4 | Fraction B-2 | 10 | <1.0E+03 |
| 5 | Fraction B-3 | 10 | <1.0E+03 |
| 6 | Fraction B-4 | 10 | <1.0E+03 |
| 7 | Fraction B-5 | 10 | 9.4E+04 |
| 8 | Fraction B-6 | 10 | 2.8E+06 |
| 9 | Fraction B-7 | 10 | 2.8E+06 |
| 10 | Fraction B-8 | 10 | 1.0E+03 |
| 11 | Fraction B-9 | 10 | 2.0E+03 |
| 12 | Fraction B-10 | 10 | <1.0E+03 |
| 13 | Fraction B-11 | 10 | <1.0E+03 |

TABLE 4-continued

| Tube # | Sample | Conc. (%) | CFU/mL |
|---|---|---|---|
| 14 | Fraction B-12 | 10 | <1.0E+03 |
| 15 | Fraction B-13 | 10 | <1.0E+03 |
| 16 | Fraction B-14 | 10 | <1.0E+03 |
| 17 | Fraction B-15 | 10 | <1.0E+03 |
| 18 | Fraction B-16 | 10 | <1.0E+03 |

Example 4

Gram-Negative and Gram-Positive Antibacterial Properties of Di(1,3-propanediol) and Di(1,2-propanediol) (DPG)

The unfractionated mixture, each fraction, a control, and DPG (comparative example) were analyzed for antibacterial or bacteristatic properties against *E. coli* according to the protocol shown below. Numbers in exponential format are indicated with "E", i.e. $2.2 \times 10^{+9}$ are written as 2.2E+09.

Figure 4:
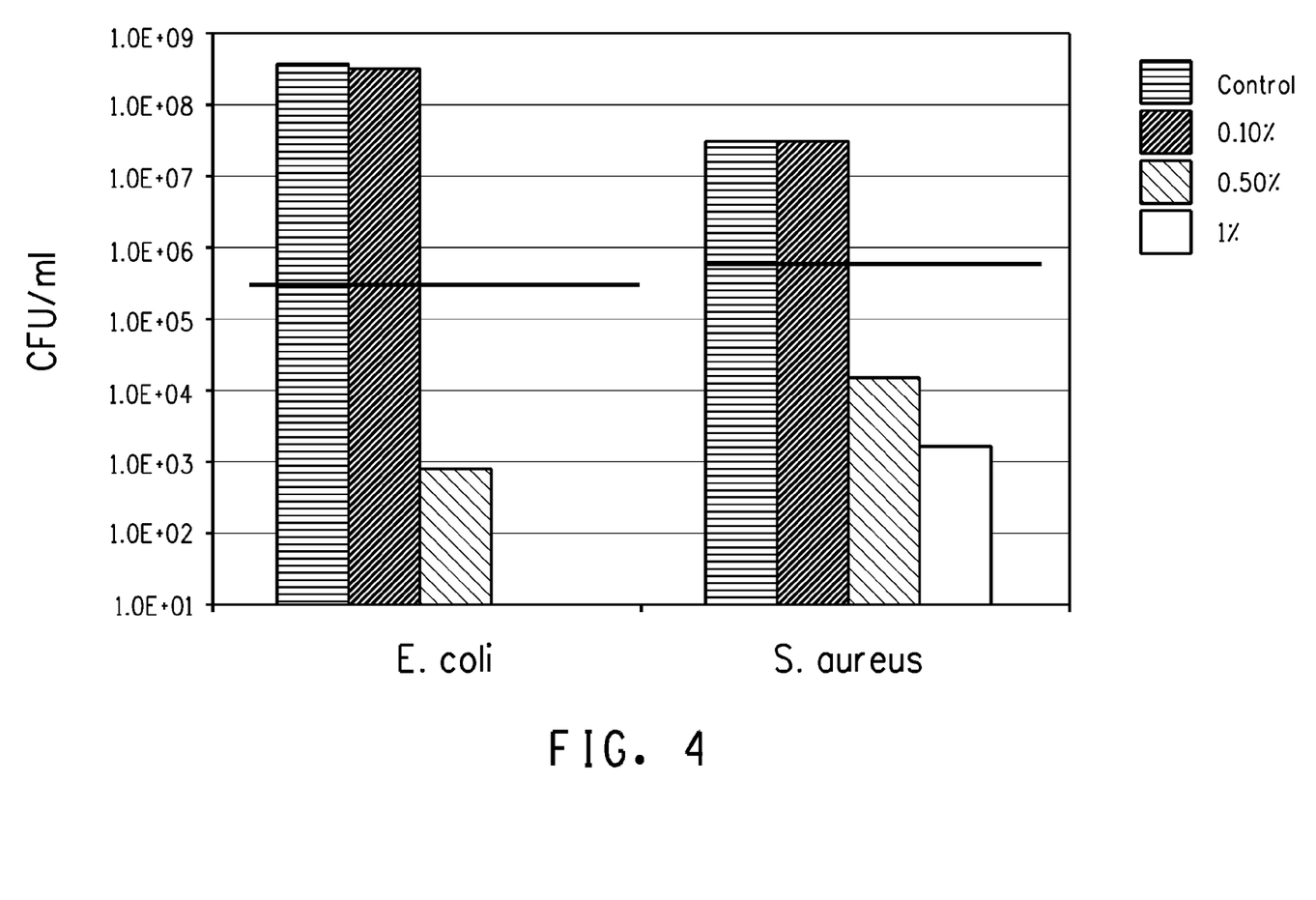
FIG. 4 shows the efficacy of trimethylene glycol dimer (di(1,3-propylene glycol)) at various concentrations against *E. coli* and *S. aureus*.
Figure 5:
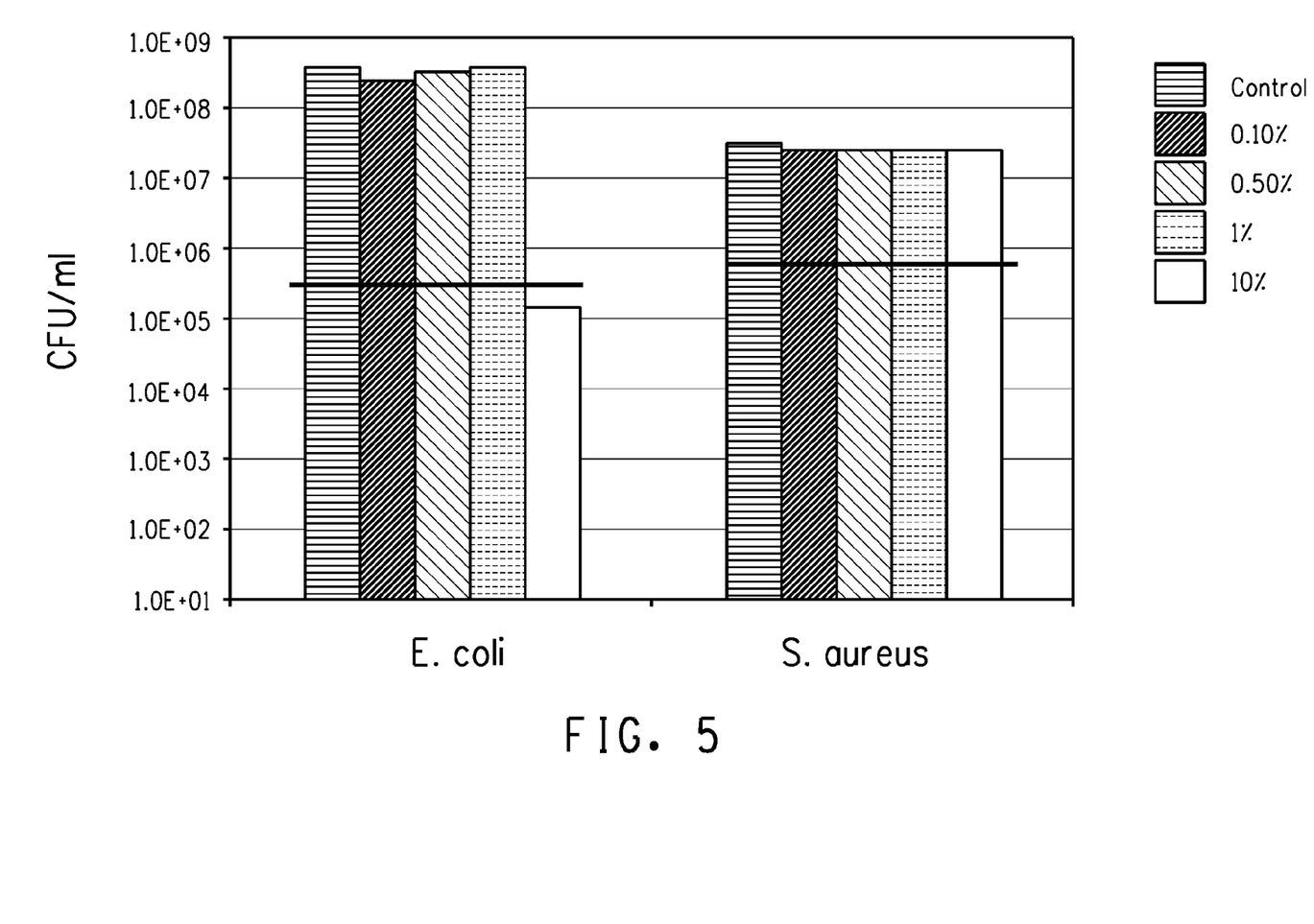
FIG. 5 shows the efficacy of di(1,2-propylene glycol) at various concentrations against *E. coli* and *S. aureus*.

The results are shown below in Table 5 below and in chart form in FIGS. 4 and 5. FIG. 4 shows the concentration of *S. aureus* and *E. coli* different concentrations of di(1,3-propanediol). The black bars indicate the conc. of both strains at the start of the incubation. This graph demonstrates that the PDO dimer at concentrations of 0.5% and 1% kills or inhibits the growth of both gram negative bacteria and gram positive bacteria. FIG. 5 shows the concentration of *S. aureus* and *E. coli* with different concs. of di(1,2-propylene glycol). The black bars indicate the conc. of both strains at the start of the incubation. This graph demonstrates that DPG shows little or no antibacterial or bacteristatic effect on gram positive bacteria.

TABLE 5

| Tube # | Sample | Conc. (%) | CFU/mL | Inoculum |
|---|---|---|---|---|
| 19 | PDO Dimer | 1 | 1.6E+03 | S. aureus |
| 20 | PDO Dimer | 0.5 | 1.4E+04 | S. aureus |
| 21 | PDO Dimer | 0.1 | 2.7E+07 | S. aureus |
| 22 | DPG | 10 | 2.1E+07 | S. aureus |
| 23 | DPG | 1 | 2.0E+07 | S. aureus |
| 24 | DPG | 0.5 | 2.0E+07 | S. aureus |
| 25 | DPG | 0.1 | 2.0E+07 | S. aureus |
| 26 | Control-2 | | 2.6E+07 | S. aureus |
| 27 | Control-3 | | 4.0E+08 | E. coli |
| 28 | PDO Dimer | 1 | <10 | E. coli |
| 29 | PDO Dimer | 0.5 | 7.6E+02 | E. coli |
| 30 | PDO Dimer | 0.1 | 3.2E+08 | E. coli |
| 31 | DPG | 10 | 1.5E+05 | E. coli |
| 32 | DPG | 1 | 3.7E+08 | E. coli |
| 33 | DPG | 0.5 | 2.9E+08 | E. coli |
| 34 | DPG | 0.1 | 2.1E+08 | E. coli |
| 35 | Control-4 | | 3.0E+08 | E. coli |

What is claimed is:

1. An antimicrobial composition comprising at least 0.1 total weight percent, based on the total weight of the composition, of two or more different trimethylene glycol oligomers of formula $R(CH_2CH_2CH_2—O)_nR^1$ wherein R is hydroxyl and $R^1$ is H, and n is 2 or higher, wherein the trimethylene glycol oligomers have an average molecular weight less than about 650, wherein the antimicrobial composition further comprising one or more additional antimicrobial additives.

2. The antimicrobial composition of claim 1 comprising at least 10 weight percent of the trimethylene glycol oligomer.

3. The antimicrobial composition of claim 1 wherein the trimethylene glycol oligomer comprises at least 0.1 weight percent of trimethylene glycol dimer.

4. A personal care or cosmetic composition comprising the antimicrobial composition of claim 1 and additionally comprising an active personal care ingredient.

5. The antimicrobial composition of claim 1 wherein the composition exhibits a reduction in antimicrobial activity of greater than 2 $\log_{10}$ against *Escherichia coli* or *Staphylococcus aureus* after 24 hours.

6. The antimicrobial composition of claim 1 wherein the trimethylene glycol oligomer is formed from biologically-derived 1,3-propanediol.

7. The antimicrobial composition of claim 1 wherein the composition comprises a mixture of dimer, trimer, and tetramer oligomers, and additionally comprises trimethylene glycol.

8. The personal care item of claim 4 that is a skin care product, liquid or powder foundation, liquid or solid eyeliner, mascara, cream eye shadow, tinted powder, perfume, deodorant, insect repellant, anesthetic, medicinal agent, mouthwash, shampoo, hair conditioner, sun care product, soap, hair anti-dandruff compositions, hair growth promoter, hair colorant, hair bleaching composition, hair anti-frizzing composition, hair relaxer, cleansing wipe, disinfecting wipe, acne treatment product, hand sanitizer, personal lubricant, skin cleanser, body lotion, hand cream, topical cream, aftershave lotion, skin toner, mouth wash, toothpaste, sunscreen lotion, baby product, diaper cream, wound healing ointment, wound covering, bandage, tape, steri-strip, medical gown, medical cap, medical face mask, medical shoe-cover, or surgical drop.

* * * * *